(12) United States Patent
Kramp et al.

(10) Patent No.: US 8,090,171 B2
(45) Date of Patent: Jan. 3, 2012

(54) IMAGE DATA SUBTRACTION SYSTEM SUITABLE FOR USE IN ANGIOGRAPHY

(75) Inventors: George F. Kramp, Elmhurst, IL (US); Gary S. Martucci, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 759 days.

(21) Appl. No.: 12/199,894

(22) Filed: Aug. 28, 2008

(65) Prior Publication Data

US 2009/0103681 A1 Apr. 23, 2009

Related U.S. Application Data

(60) Provisional application No. 60/981,226, filed on Oct. 19, 2007.

(51) Int. Cl.
*G06K 9/00* (2006.01)

(52) U.S. Cl. ........ 382/128; 382/130; 382/131; 382/132; 378/4; 378/8

(58) Field of Classification Search .................. 382/128, 382/130; 378/8, 98.11
See application file for complete search history.

(56) References Cited

U.S. PATENT DOCUMENTS

| | | | | |
|---|---|---|---|---|
| 4,437,161 A | * | 3/1984 | Anderson | 600/425 |
| 4,542,459 A | * | 9/1985 | Riederer | 600/431 |
| 4,723,261 A | * | 2/1988 | Janssen et al. | 378/98.5 |
| 5,018,173 A | * | 5/1991 | Komai et al. | 378/4 |
| 5,644,613 A | * | 7/1997 | Mick | 378/98.12 |
| 6,370,417 B1 | * | 4/2002 | Horbaschek et al. | 600/424 |
| 6,647,283 B2 | * | 11/2003 | Klotz | 600/425 |
| 7,269,246 B2 | | 9/2007 | Ohishi | |
| 7,313,216 B2 | * | 12/2007 | Nishide et al. | 378/15 |
| 7,330,573 B2 | | 2/2008 | Mielekamp | |
| 7,333,648 B2 | | 2/2008 | Edic et al. | |
| 7,412,023 B2 | * | 8/2008 | Ohishi et al. | 378/4 |
| 7,953,263 B2 | * | 5/2011 | Okamoto et al. | 382/128 |
| 2005/0100208 A1 | | 5/2005 | Suzuki et al. | |
| 2007/0195932 A1 | | 8/2007 | Nakaura et al. | |
| 2008/0037844 A1 | | 2/2008 | Baumgart | |
| 2008/0051648 A1 | | 2/2008 | Suri et al. | |

\* cited by examiner

*Primary Examiner* — Alexander H Taningco
(74) *Attorney, Agent, or Firm* — Alexander J Burke

(57) ABSTRACT

An image data subtraction system suitable for use in Angiography or other medical procedure enhances vessel visualization. The system comprises an imaging system for acquiring, during a medical procedure, data representing multiple temporally sequential individual images of vessels of a portion of patient anatomy. The sequential individual images encompass introduction of a contrast agent. An image processor automatically processes the data representing the multiple temporally sequential individual images to identify a first image indicating presence of the contrast agent and a second image preceding the first image by comparing a difference between measures representative of luminance content of the first and second image, with a threshold. The second image is substantially exclusive of an indication of presence of the contrast agent. The image processor, in response to the difference exceeding the threshold, automatically selects the second image as a mask image and subtracts data representing the mask image from data representing images of the temporally sequential individual images to remove background image detail and emphasize vessel structure in providing processed image data for display. A user interface presents the processed image data for display while the patient is undergoing the medical procedure.

11 Claims, 5 Drawing Sheets

Frame 1　Frame 2　Frame 3　Frame 4　Frame 5　Frame 6

IMAGE DATA SUBTRACTION SYSTEM SUITABLE FOR USE IN ANGIOGRAPHY

This is a non-provisional application of provisional application Ser. No. 60/981,226 filed Oct. 19, 2007, by G. F. Kramp et al.

FIELD OF THE INVENTION

This invention concerns an image data subtraction system suitable for use in Angiography to enhance vessel visualization involving automatic identification and subtraction of a mask image from other images to remove background image detail and emphasize vessel structure while a patient is undergoing Angiography, for example.

BACKGROUND OF THE INVENTION

Digital Subtraction Angiography (DSA) is a known process employed in angiography imaging applications in radiology to remove background anatomical data which distracts from clinically relevant vessel structure of a patient. For example, in neuro-radiological imaging studies, a physician may desire to see the vessel structure of a patient brain without being obscured by the boney structure of the skull. In performing a DSA process, a single mask frame (containing background anatomical detail for removal from images) is selected from a scene and subtracted from the image frames. FIG. 1 illustrates subtraction of Mask image data 107 from corresponding Fill image data 105 to provide desired DSA image data 103.

A Mask image frame is typically selected by a known laboratory information system in response to a determination that a regulated patient dose of the x-ray field has been completed. The Mask image frame in known systems is selected in a virtually arbitrary fashion based upon laboratory conditions irrespective of image quality and may often be less than optimal, resulting in the burden of selection of a new Mask image frame. The selection of a new Mask image frame is typically performed in a post-processing operation, when a patient procedure has already been completed and the patient is no longer present. Therefore, in known systems the enhanced image quality provided by new and more accurate Mask image selection occurs too late to improve guidance to a physician performing a radiological procedure on a patient. A system according to invention principles addresses these deficiencies and related problems.

SUMMARY OF THE INVENTION

A system provides substantially real-time automatic, accurate selection of a mask image frame in response to image content while a patient is undergoing a medical procedure. An image data subtraction system suitable for use in Angiography or other medical procedure enhances vessel visualization. The system comprises an imaging system for acquiring, during a medical procedure, data representing multiple temporally sequential individual images of vessels of a portion of patient anatomy. The sequential individual images encompass introduction of a contrast agent. An image processor automatically processes the data representing the multiple temporally sequential individual images to identify a first image indicating presence of the contrast agent and a second image preceding the first image by comparing a difference between measures representative of luminance content of the first and second image, with a threshold. The second image is substantially exclusive of an indication of presence of the contrast agent. The image processor, in response to the difference exceeding the threshold, automatically selects the second image as a mask image and subtracts data representing the mask image from data representing images of the temporally sequential individual images to remove background image detail and emphasize vessel structure in providing processed image data for display. A user interface presents the processed image data for display while the patient is undergoing the medical procedure.

DETAILED DESCRIPTION OF THE INVENTION

Figure 1:
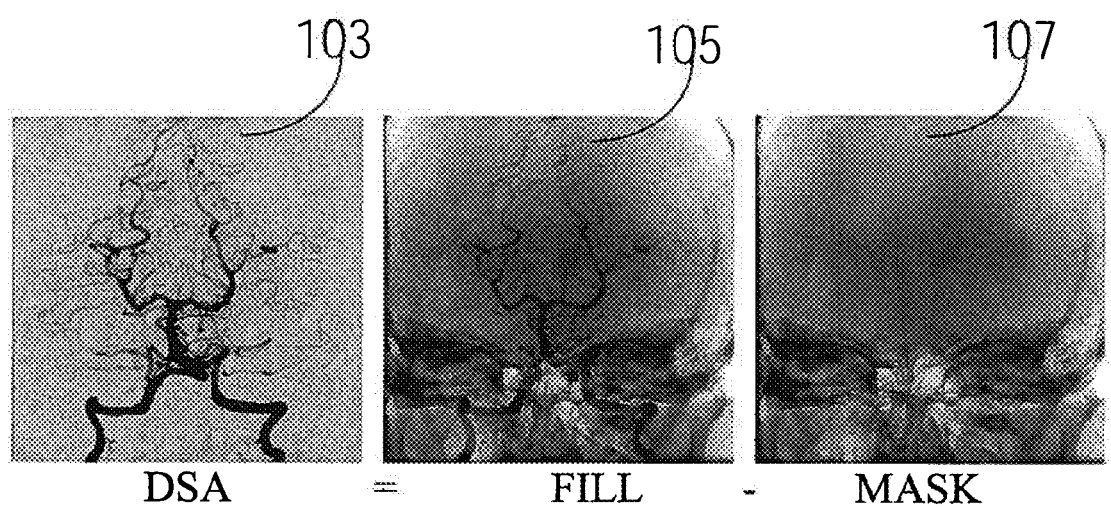
FIG. 1 illustrates a known Digital Subtraction Angiography process involving subtraction of a Mask image from a Medical image.

A system provides substantially real-time automatic, accurate selection of a mask image frame in response to image content while a patient is undergoing a medical procedure. The system automatically detects an image frame by identifying a medical imaging modality device image including an artifact (e.g., indicating presence of a contrast agent, catheter or stent, for example). In response to the image detection, the system selects an image excluding the artifact that precedes the detected image for use as a Mask image while a patient is undergoing a medical procedure. The system advantageously subtracts data representative of the selected Mask image from data representative of medical images used by a physician in performing a medical procedure (such as an Angiography procedure), while a patient is undergoing the procedure. In contrast in known systems, a non-optimal Mask image is selected or a Mask image is selected in an image post-processing operation after performance of a medical procedure that was performed using reduced quality medical images derived using a non-optimally selected Mask image. The known system Mask image selection in an image post-processing operation is too late to improve guidance to a physician performing a radiological procedure on a patient, for example.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 5) herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

Figure 2:
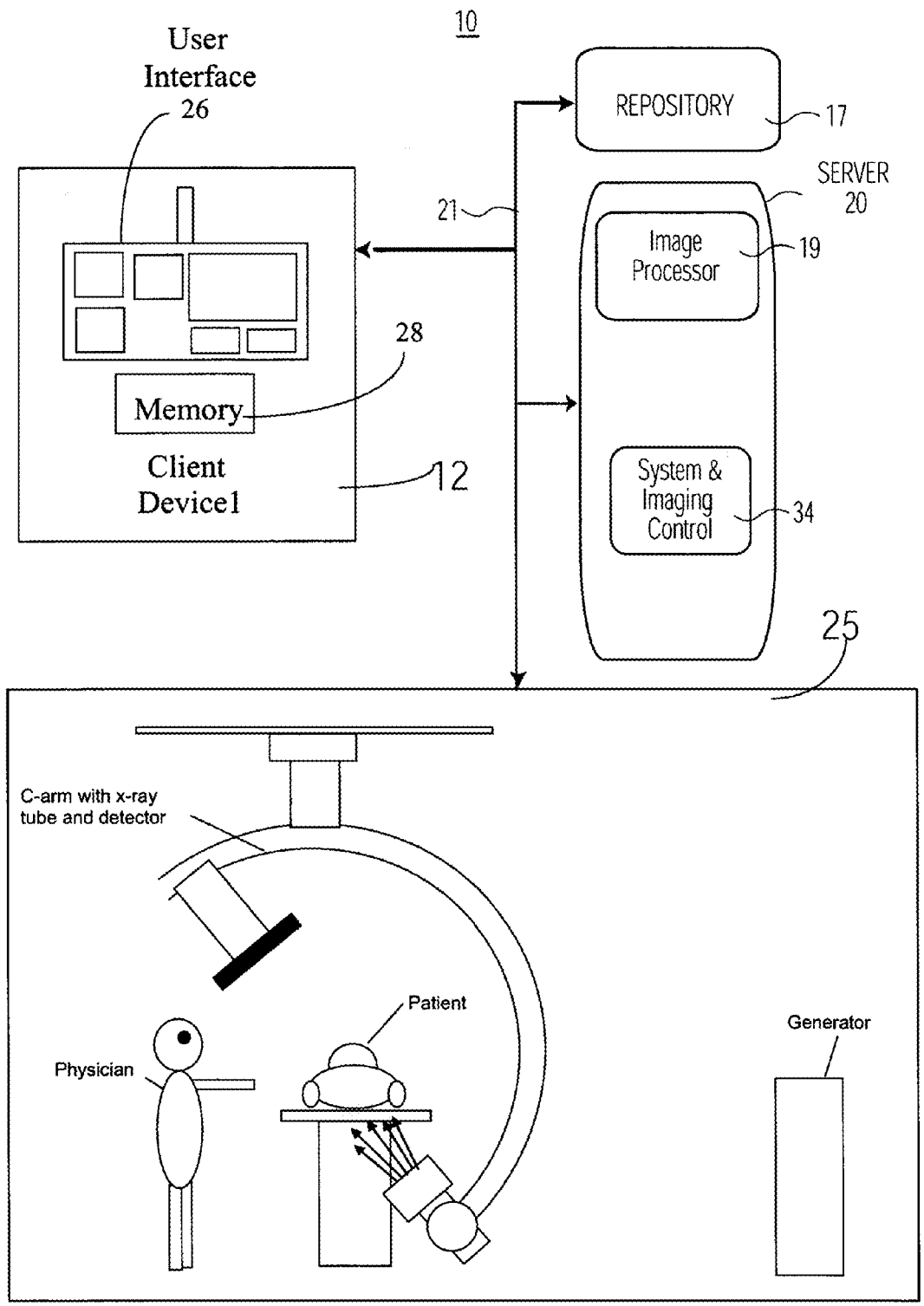
FIG. 2 shows an image data subtraction system suitable for use in Angiography or other medical procedure to enhance vessel visualization, according to invention principles.

FIG. 2 shows X-ray imaging system 10 including an image data subtraction system suitable for use in Angiography or other medical procedure to enhance vessel visualization. System 10 includes one or more processing devices (e.g., workstation or portable device such as notebooks, Personal Digital Assistants, phones) 12 that individually include a user interface 26 supporting image presentation in response to predetermined user (e.g., physician) specific preferences and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. User interface 26 provides data representing display images comprising a Graphical User Interface (GUI) for presentation on processing device 12. At least one repository 17 stores medical image studies for multiple patients in DICOM compatible (or other) data format. A medical image study individually includes multiple image series of a patient anatomical portion which in turn individually include multiple images. Server 20 includes image processor 19 and system and imaging controller 34.

The image data subtraction system is suitable for use in Angiography (catheterization and stent manipulation) or other medical procedure to enhance vessel visualization. Imaging system 10 acquires, during a medical procedure, data representing multiple temporally sequential individual images of vessels of a portion of patient anatomy using X-ray modality system 25. X-ray modality system 25 comprises a C-arm X-ray radiation source and detector device rotating about a patient table and an associated electrical generator for providing electrical power for the X-ray radiation system. The sequential individual images encompass introduction of a contrast agent (or interventional device). Image processor 19 automatically, processes the data representing the multiple temporally sequential individual images to identify a first image indicating presence of the contrast agent (or interventional device) and a second image preceding the first image by comparing a difference between measures representative of luminance content of the first and second image, with a threshold. The second image is substantially exclusive of an indication of presence of the contrast agent (or interventional device). In response to the difference exceeding the threshold, image processor 19 automatically selects the second image as a mask image and subtracts data representing the mask image from data representing images of the temporally sequential individual images to remove background image detail and emphasize vessel structure in providing processed image data for display. User interface 26 presents the processed image data for display while the patient is undergoing the medical procedure. The interventional device comprises a stent or a catheter, for example.

Figure 3:
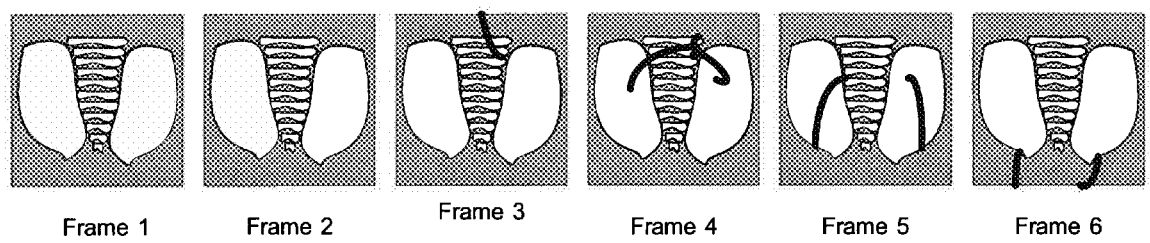
FIG. 3 illustrates an image sequence from which a Mask image is selected, according to invention principles.

FIG. 3 illustrates an image sequence from which a Mask image is selected. Image processor 19 (FIG. 1) advantageously selects a mask image in response to image content rather than contrast agent dose regulation, for example. In one embodiment, image processor 19 automatically selects a new mask after a new image series is acquired by X-ray imaging modality system 25 and before the series is stored in a local repository such as repository 17. Image processor 19 automatically identifies a first image in a sequence of images in which a contrast agent enters the field of view as illustrated in image Frame 3 and selects prior image (Frame 2) as a mask frame. Image processor 19 derives measures representative of luminance content of the image frames and compares differences between the measures of successive image frames. Image processor 19 determines a frame indicates introduction of a contrast agent or interventional device (e.g., a catheter, stent) in response to a difference exceeding a predetermined threshold. In other embodiments a variety of different image comparison processes may be used to compare images and identify an image frame that indicates introduction of a contrast agent or interventional device.

Upon selection of a mask image frame, the selected mask image frame is made immediately available for use in removing (subtracting) undesired background detail from medical images acquired during an imaging examination while the examination is being performed and the patient is present. The mask image is also available for other medical image post processing functions which a user may perform either using medical X-ray imaging system 25 or after transfer of acquired medical images to a post processing workstation. In a further embodiment, image processor 19 automatically selects a new mask during acquisition of a new image series by X-ray imaging modality system 25 and/or during or after storage of the image series in repository 17.

FIG. 3 illustrates entry of a contrast agent into anatomical vessels of a patient in image frame 3 which initiates image processor 19 to select image frame 2 as a mask image. In one embodiment image processor 19 derives a histogram as a measure representative of luminance content of the image frames and compares differences between the histogram measures of successive image frames. In the histogram, a horizontal axis represents each luminance pixel value possible from black to white. The vertical axis indicates values representing the number of pixels in the image that occur at each luminance pixel value level. Image processor 19 generates and analyzes histograms for a Region of Interest (ROI) of individual image frames. The ROI may be determined arbitrarily via predetermined configuration data, or by using a field of view (FOV) area within a collimation to limit the ROI, or a combination of both. Image processor 19 processes the pixel data within the determined ROI to derive the ROI pixel luminance (e.g., grayscale) distribution comprising a histogram.

Figure 4:
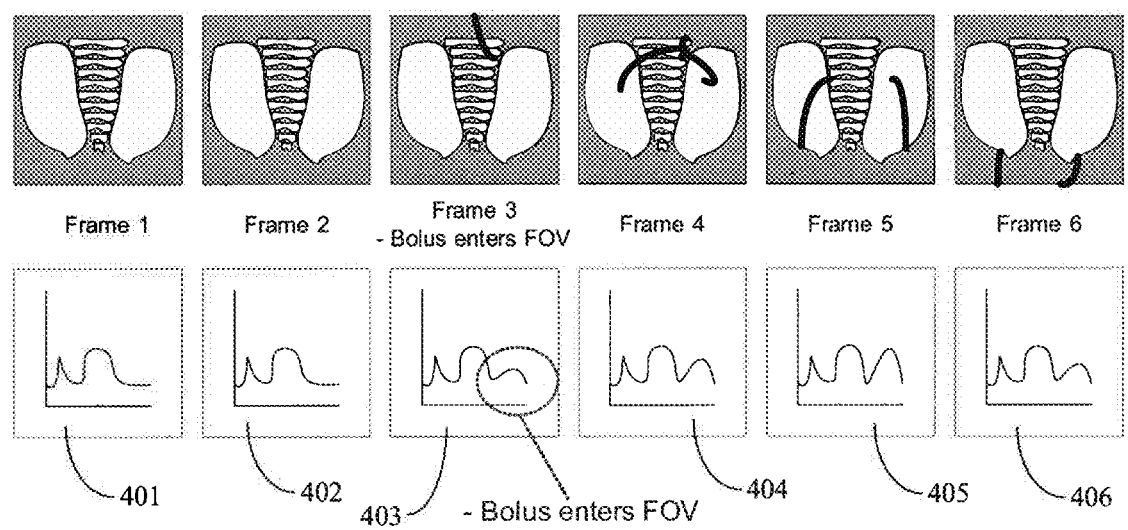
FIG. 4 illustrates detection of an image including an artifact associated with a medical procedure employed in selecting a Mask image, according to invention principles.

FIG. 4 illustrates detection by image processor 19 of an image including an artifact associated with a medical procedure employed in selecting a Mask image. Image processor 19 processes the pixel data within the determined ROI for image frames 1-6 to derive the ROI pixel luminance (e.g., grayscale) distributions shown in corresponding histograms 401, 402, 403, 404, 405 and 406. Image processor 19 compares and correlates histogram data representing successive images of a medical image sequence of a patient anatomical portion to identify a first image of a sequence in which change of luminance data (e.g., increased darkness representing Iodine contrast agent) occurs in the sequence to determine when the contrast agent enters the ROI. In response to determining a difference in measures representative of luminance content (histograms) of image frames 2 and 3 exceeds a predetermined threshold, processor 19 identifies image frame 3 as the first image of the sequence in which contrast agent enters the ROI. Image processor 19 further selects image frame 2 comprising the image frame immediately preceding image frame 3 as the Mask image. Processor 19 initiates image comparison after administration of the contrast agent to ensure that there is sufficient background image variation for acquiring histogram data for comparison and correlation.

Figure 5:
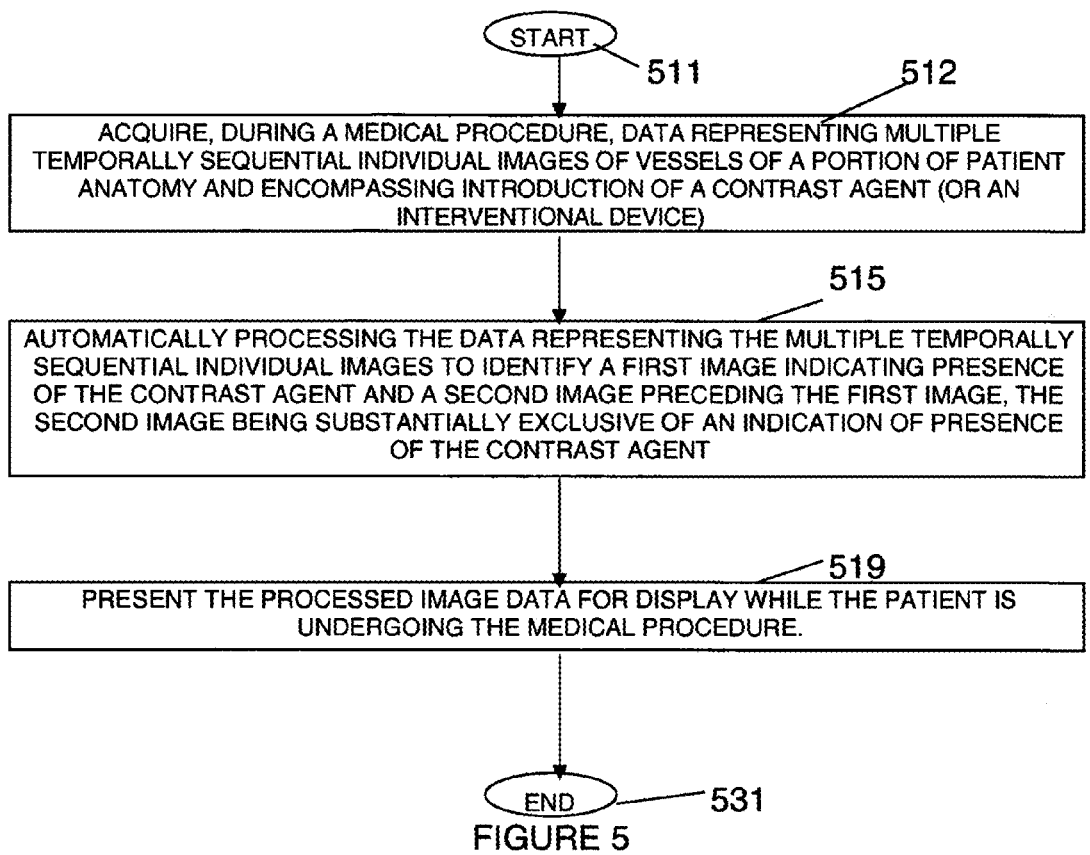
FIG. 5 shows a flowchart of a process performed by an image data subtraction system suitable for use in Angiography or other medical procedure to enhance vessel visualization, according to invention principles.

FIG. 5 shows a flowchart of a process performed by an image data subtraction system in system 10 suitable for use in Angiography or other medical procedure to enhance vessel visualization. In step 512, following the start at step 511, imaging system 25 (FIG. 2) acquires, during a medical procedure, data representing multiple temporally sequential individual images of vessels of a portion of patient anatomy in which the sequential individual images encompass introduction of a contrast agent (or in another embodiment, an interventional device such as a catheter or stent, for example).

In step 515, image processor 19 automatically, processes the data representing the multiple temporally sequential individual images to identify a first image indicating presence of the contrast agent (or interventional device) and a second image that (e.g., substantially immediately) precedes the first image and is substantially exclusive of an indication of presence of the contrast agent (or interventional device). Image processor 19 does this by comparing a difference between measures representative of luminance content of the first and second image, with a threshold. In response to the difference exceeding the threshold, image processor 19 selects the second image as a mask image and subtracts data representing the mask image from data representing images of the temporally sequential individual images to remove background image detail and emphasize vessel structure in providing processed image data for display. Image processor 19 derives measures representative of luminance content of the first and second image using at least one of multiple different processes including by generating a histogram derived from pixel grayscale values.

In one embodiment, image processor 19 processes the data representing the multiple temporally sequential individual images to identify a first plurality of images preceding the first image that are substantially exclusive of an indication of presence of the contrast agent (or interventional device) and selects the second image from the first plurality of images. Similarly, image processor 19 processes the data representing the multiple temporally sequential individual images to identify a second plurality of images indicating presence of the contrast agent (or interventional device) and selects the first image from the second plurality of images. Image processor 19, in one embodiment, dynamically substitutes the mask image for a previously used mask image selected by a default process, for example. In step 519, user interface 26 presents the processed image data for display while the patient is undergoing the medical procedure. The process of FIG. 5 terminates at step 531.

The systems and processes of FIGS. 2-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The image data subtraction system is suitable for use with a wide variety of imaging devices including X-ray, MR, CT scan, Ultrasound, nuclear scanning employed in Angiography or another medical procedure to enhance vessel visualization. The processes and applications may, in alternative embodiments, be located on one or more (e.g., distributed) processing devices accessing a network linking the elements of FIG. 2. Further, any of the functions and steps provided in FIGS. 2-5 may be implemented in hardware, software or a combination of both and may reside on one or more processing devices located at any location of a network linking the elements of FIG. 2 or another linked network, including the Internet.

What is claimed is:

1. An image data subtraction system suitable for use in Angiography or other medical procedure to enhance vessel visualization, comprising:

an imaging system for acquiring, during a medical procedure, data representing a plurality of temporally sequential individual images of vessels of a portion of patient anatomy, said sequential individual images encompassing introduction of a contrast agent;

an image processor for automatically, processing said data representing said plurality of temporally sequential individual images to identify, a first image indicating presence of said contrast agent, and a second image preceding said first image, by comparing a difference between measures representative of luminance content of the first and second image, with a threshold, said image processor identifying a first plurality of images preceding said first image and being substantially exclusive of an indication of presence of said contrast agent and selecting said second image from the first plurality of images and in response to said difference exceeding said threshold, selecting said second image as a mask image and subtracting data representing said mask image from data representing images of said temporally sequential individual images to remove background image detail and emphasize vessel structure in providing processed image data for display; and a user interface for presenting said processed image data for display while said patient is undergoing said medical procedure.

2. A system according to claim 1, wherein
said second image substantially immediately precedes said first image.

3. A system according to claim 1, wherein
said image processor dynamically substitutes said mask image for a previously used mask image.

4. A system according to claim 3, wherein
said previously used mask image is a mask image selected by a default process.

5. A system according to claim 1, wherein
said image processor identifies said first plurality of images by comparing a difference between measures representative of luminance content of the first image and sad first plurality of images, with a threshold.

6. A system according to claim 1, wherein
said image processor processes said data representing said plurality of temporally sequential individual images to identify a second plurality of images indicating presence of said contrast agent and selects said first image from the second plurality of images.

7. A system according to claim 1, wherein
said image processor derives measures representative of luminance content of said first and second image using at least one of a plurality of different processes.

8. A system according to claim 7, wherein
said at least one of said plurality of different processes comprises a histogram derived from pixel grayscale values.

9. An image data subtraction system suitable for use in Angiography or other medical procedure to enhance vessel visualization, comprising:

an imaging system for acquiring, during a medical procedure, data representing a plurality of temporally sequential individual images of vessels of a portion of patient anatomy, said sequential individual images encompassing introduction of an interventional device;

an image processor for automatically,
processing said data representing said plurality of temporally sequential individual images to identify,
a first image indicating presence of said interventional device and
a second image preceding said first image, by comparing a difference between measures representative of luminance content of the first and second image, with a threshold, said image processor selecting said second image from a plurality of images preceding said first image and being substantially exclusive of an indication of presence of said interventional device and in response to said difference exceeding said threshold, selecting said second image as a mask image and subtracting data representing said mask image from data representing images of said temporally sequential individual images to remove background image detail and emphasize vessel structure in providing processed image data for display; and a user interface for presenting said processed image data for display while said patient is undergoing said medical procedure.

10. A system according to claim 9, wherein
said interventional device comprises at least one of, (a) a stent and (b) a catheter.

11. An image data subtraction method suitable for use in Angiography or other medical procedure to enhance vessel visualization, comprising the activities of:

acquiring, during a medical procedure, data representing a plurality of temporally sequential individual images of vessels of a portion of patient anatomy, said sequential individual images encompassing introduction of a contrast agent;

automatically,
processing said data representing said plurality of temporally sequential individual images to identify,
a first image indicating presence of said contrast agent and
a second image preceding said first image, by comparing a difference between measures representative of luminance content of the first and second image, with a threshold, said image processor selecting said second image from a plurality of images preceding said first image and being substantially exclusive of an indication of presence of said contrast agent and in response to said difference exceeding said threshold, selecting said second image as a mask image and subtracting data representing said mask image from data representing images of said temporally sequential individual images to remove background image detail and emphasize vessel structure in providing processed image data for display; and presenting said processed image data for display while said patient is undergoing said medical procedure.

* * * * *